(12) United States Patent
Uhr et al.

(10) Patent No.: US 8,048,903 B2
(45) Date of Patent: Nov. 1, 2011

(54) 5-IODOTETRAZOLES

(75) Inventors: Hermann Uhr, Leverkusen (DE);
Rainer Bruns, Leverkusen (DE);
Erasmus Vogl, Leverkusen (DE);
Martin Kugler, Leichlingen (DE);
Oliver Kretschik, Pittsburgh, PA (US);
Bernhard Neumann, Saale (DE)

(73) Assignee: LANXESS Deutschland GmbH, Leverkusen (DE)

( * ) Notice: Subject to any disclaimer, the term of this patent is extended or adjusted under 35 U.S.C. 154(b) by 651 days.

(21) Appl. No.: 11/658,202

(22) PCT Filed: Jul. 19, 2005

(86) PCT No.: PCT/EP2005/007824
§ 371 (c)(1),
(2), (4) Date: Aug. 27, 2008

(87) PCT Pub. No.: WO2006/012996
PCT Pub. Date: Feb. 9, 2006

(65) Prior Publication Data
US 2009/0036506 A1    Feb. 5, 2009

(30) Foreign Application Priority Data
Jul. 30, 2004   (DE) .......................... 10 2004 037 366

(51) Int. Cl.
*A61K 31/41*        (2006.01)
*C07D 257/04*       (2006.01)
(52) U.S. Cl. .......................... 514/381; 548/250; 548/252
(58) Field of Classification Search .................. 514/381; 548/250, 252
See application file for complete search history.

(56) References Cited

U.S. PATENT DOCUMENTS

| 6,143,204 A | 11/2000 | Lutz et al. | 252/384 |
|---|---|---|---|
| 6,353,021 B1 | 3/2002 | Gaglani et al. | 514/478 |
| 2006/0013833 A1 | 1/2006 | Bartko | 424/400 |

FOREIGN PATENT DOCUMENTS
WO   2007/028527   3/2007

OTHER PUBLICATIONS

Copending U.S. Appl. No. 11/922,426, filed 2007.*
Jacobson, et al., J.O.C., 1954, vol. 19, pp. 1652-1661.*
C.A. Jacobson et al; J. Org. Chem. 1954, 19, 1652 XP-002351055 "Tetrazole chemistry. II. The Synthesis and reactions of 1-phenyl-5-acetyltetrazole".
F.W. Fowler et al; J. Am. Chem. Soc. 1967, 89, 2077-2082 "Stereospecific Introduction of Azide Functions into Organic Molecules".
W.L. Collibee etal; J. Org. Chem. 1995, 60, 468-469 "5-Halo-1-phenyltetrazoles".
R. Rapp, Can. J. Chem. 1971, 49, 2139-2142 "Reactions of 1-Substituted 5-Tetrazolyllithium Compounds; Preparation of 5-Substituted 1-Methyltetraxoles".
Satoh, Yoshiaka; Tetrahedron Lett., 1995, 36, 1759 XP-002351051 Application of 5-lithiotetrazoles Inorganic systhesis.
Satoh, Yoshitaka, Synlett 1998, 528-530 "Homologation of 1-(Benzyloxymethyl)-1*H*-tetrazole via Lithiation".
P.N. Gaponik, Khimiya Geterotsiklicheskikh Soedinenii 1988, 1699 XP-002351053.

* cited by examiner

*Primary Examiner* — Kamal Saeed
*Assistant Examiner* — Kristin Bianchi
(74) *Attorney, Agent, or Firm* — Nicanor A. Kohncke

(57) ABSTRACT

The compounds of the formula (I)

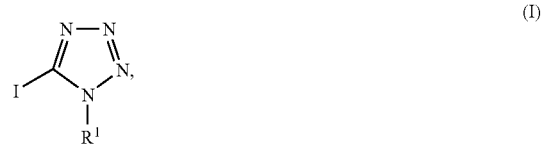

in which
$R^1$ represents hydrogen or in each case optionally substituted alkyl, alkenyl, alkynyl or phenyl are highly suitable as microbicides for protecting plants and materials.

4 Claims, No Drawings

5-IODOTETRAZOLES

The invention relates to the use of novel and known 5-iodotetrazoles as biocides for protecting plants and industrial materials, to novel 5-iodotetrazoles and to processes for their preparation.

Some iodotetrazoles and routes for their preparation are already known from the literature. A biological action is not mentioned in any of the prior-art examples.

The preparation of 5-iodo-1-phenyltetrazole from 5-acetyl-1-phenyltetrazole and sodium hypoiodite is known (cf. C. A. Jacobson et al., J. Org. Chem. 1954, 19, 1652).

A further way to prepare 5-iodo-1-phenyltetrazole from phenylisonitrile and $IN_3$ has been described (cf. F. W. Fowler et al.; J. Am. Chem. Soc. 1967, 89, 2077; W. L. Collibee et al., J. Org. Chem. 1995, 60, 468).

5-Iodotetrazoles can also be obtained by reacting 1-substituted 5-tetrazolyllithium compounds at low temperatures with iodine (cf. R. Raap, Can. J. Chem. 1971, 49, 2139; Satoh, Yoshitaka; Tetrahedron Lett., 1995, 36, 1759; Satoh, Yoshitaka, Synlett 1998, 528).

A further process for preparing 1-alkyl-5-iodotetrazoles uses 1-alkyltetrazoles as starting materials which are treated with iodine in glacial acetic acid containing $KMnO_4$ and $H_2SO_4$ (cf. P. N. Gaponik, Khimiya Geterotsiklicheskikh Soedinenii 1988, 1699).

It has now been found that certain 5-iodotetrazoles which are substituted in the 1-position are highly suitable as microbicides for protecting plants and materials.

Accordingly, the present invention provides the use of compounds of the formula (I)

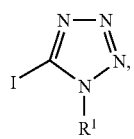

(I)

in which
$R^1$ represents hydrogen or in each case optionally substituted alkyl, alkenyl, alkynyl or phenyl as microbicides for protecting plants and materials.

Preference is given to using compounds of the general formula (I), in which
  $R^1$ represents hydrogen, represents straight-chain or branched $C_1$-$C_8$-alkyl which is unsubstituted or mono- or polysubstituted by identical or different substituents, represents straight-chain or branched $C_2$-$C_8$-alkenyl which is unsubstituted or mono- or polysubstituted by identical or different substituents or represents straight-chain or branched $C_2$-$C_8$-alkynyl which is unsubstituted or mono- or polysubstituted by identical or different substituents,
  where the substituents for the alkyl, alkenyl and alkynyl radicals which are mono- or polysubstituted by identical or different substituents are selected from the group consisting of halogen; nitro; cyano; hydroxyl; unsubstituted $C_1$-$C_6$-alkoxy; $C_1$-$C_6$-alkoxy which is mono- to nonasubstituted by identical or different halogen substituents; unsubstituted $C_1$-$C_6$-alkylthio; $C_1$-$C_6$-alkylthio which is mono- to nonasubstituted by identical or different halogen substituents; amino; monoalkylamino having straight-chain or branched $C_1$-$C_6$-alkyl radicals; dialkylamino having identical or different straight-chain or branched $C_1$-$C_6$-alkyl radicals; unsubstituted phenyl; phenyl which is mono- to pentasubstituted by identical or different substituents from the group consisting of halogen, nitro, cyano, alkyl, haloalkyl, alkoxy, haloalkoxy, alkylthio, haloalkylthio, acyl, acyloxy, alkoxycarbonyl, carboxyl, amino, monoalkylamino and dialkylamino;
or
  $R^1$ represents unsubstituted phenyl or represents phenyl which is mono- to pentasubstituted by identical or different substituents from the group consisting of halogen, nitro, cyano, hydroxyl, alkyl, haloalkyl, alkoxy, haloalkoxy, alkylthio, haloalkylthio, acyl, acyloxy, alkoxycarbonyl, carboxyl, amino, monoalkylamino and dialkylamino.

Particular preference is given to using compounds of the general formula (I) in which
  $R^1$ represents hydrogen, represents straight-chain or branched $C_1$-$C_8$-alkyl which is unsubstituted or mono- to tetrasubstituted by identical or different substituents, represents $C_2$-$C_6$-alkenyl which is unsubstituted or mono- to tetrasubstituted by identical or different substituents or represents $C_2$-$C_6$-alkynyl which is unsubstituted or mono- to tetrasubstituted by identical or different substituents,
    where the substituents for the $C_1$-$C_8$-alkyl, $C_2$-$C_6$-alkenyl und $C_2$-$C_6$-alkynyl radicals which are mono- to tetrasubstituted by identical or different substituents are selected from the group consisting of fluorine; chlorine; bromine; nitro; cyano; hydroxyl; unsubstituted $C_1$-$C_4$-alkoxy; $C_1$-$C_4$-alkoxy which is mono- to pentasubstituted by identical or different substituents from the group consisting of fluorine, chlorine and bromine; unsubstituted $C_1$-$C_4$-alkylthio; $C_1$-$C_4$-alkylthio which is mono- to pentasubstituted by identical or different substituents from the group consisting of fluorine, chlorine and bromine; amino; monoalkylamino having straight-chain or branched $C_1$-$C_4$-alkyl radicals; dialkylamino having identical or different straight-chain or branched $C_1$-$C_4$-alkyl radicals; unsubstituted phenyl; phenyl which is mono- to tetrasubstituted by identical or different substituents from the group consisting of fluorine, chlorine, bromine, nitro, cyano, hydroxyl, $C_1$-$C_4$-alkyl, $C_1$-$C_4$-haloalkyl which is mono- to pentasubstituted by identical or different substituents from the group consisting of fluorine, chlorine and bromine, $C_1$-$C_4$-alkoxy, $C_1$-$C_4$-haloalkoxy which is mono- to pentasubstituted by identical or different substituents from the group consisting of fluorine, chlorine and bromine, $C_1$-$C_4$-alkylthio, $C_1$-$C_4$-haloalkylthio which is mono- to pentasubstituted by identical or different substituents from the group consisting of fluorine, chlorine and bromine, $C_1$-$C_6$-acyl, $C_1$-$C_6$-acyloxy, $C_1$-$C_6$-alkoxycarbonyl, carboxyl, amino, monoalkylamino having straight-chain or branched $C_1$-$C_4$-alkyl radicals, dialkylamino having identical or different straight-chain or branched $C_1$-$C_4$-alkyl radicals,
or
  $R^1$ represents unsubstituted phenyl or represents phenyl which is mono- to tetrasubstituted by identical or different substituents from the group consisting of fluorine, chlorine, bromine, nitro, cyano, hydroxyl, $C_1$-$C_4$-alkyl, $C_1$-$C_4$-haloalkyl which is mono- to pentasubstituted by identical or different substituents from the group consisting of fluorine, chlorine and bromine, $C_1$-$C_4$-alkoxy, $C_1$-$C_4$-haloalkoxy which is mono- to pentasubstituted by identical or different substituents from the group consisting of fluorine, chlorine and bromine, $C_1$-$C_4$-alkylthio, $C_1$-$C_4$-haloalkylthio which is mono- to pentasubstituted by identical or different substituents from the group consisting of fluorine, chlorine and bromine, $C_1$-$C_4$-acyl, $C_1$-$C_4$-acyloxy, $C_1$-$C_4$-alkoxycarbonyl, carboxyl, amino, monoalkylamino having straight-chain or branched $C_1$-$C_4$-alkyl radicals, dialkylamino having identical or different straight-chain or branched $C_1$-$C_4$-alkyl radicals.

Very particular preference is given to using compounds of the formula (I) in which $R^1$ represents hydrogen, methyl, ethyl, n-propyl, isopropyl, n-butyl, isobutyl, sec-butyl, tert-butyl, n-pentyl, n-hexyl, n-heptyl, n-octyl, allyl, vinyl, propargyl, where the alkyl radicals mentioned are in each case optionally mono- to tetrasubstituted by identical or different substituents from the group consisting of fluorine, chlorine, bromine, nitro, cyano, hydroxyl, methoxy, ethoxy, n-propoxy, isopropoxy, n-butoxy, isobutoxy, sec-butoxy, tert-butoxy, trifluoromethoxy, methylthio, ethylthio, n-propylthio, isopropylthio, trifluoromethylthio, amino, methylamino, ethylamino, n-propylamino, isopropylamino, dimethylamino, diethylamino, methylethylamino, di-n-propylamino, diisopropylamino, unsubstituted phenyl, phenyl which is mono- to trisubstituted by fluorine, chlorine, bromine, nitro, cyano, hydroxyl, methyl, ethyl, n-propyl, isopropyl, n-butyl, isobutyl, s-butyl, tert-butyl, trifluoromethyl, methoxy, ethoxy, n-propoxy, isopropoxy, n-butoxy, isobutoxy, sec-butoxy, tert-butoxy, trifluoromethoxy, methylthio, ethylthio, n-propylthio, isopropylthio, trifluoromethylthio, formyl, acetyl, acetyloxy, methoxycarbonyl, ethoxycarbonyl, carboxyl, amino, methylamino, ethylamino, n-propylamino, isopropylamino, dimethylamino, diethylamino, methylethylamino, di-n-propylamino, diisopropylamino, or $R^1$ represents unsubstituted phenyl or represents phenyl which is mono- to trisubstituted by fluorine, chlorine, bromine, nitro, cyano, hydroxyl, methyl, ethyl, n-propyl, isopropyl, n-butyl, isobutyl, s-butyl, tert-butyl, trifluoromethyl, methoxy, ethoxy, n-propoxy, isopropoxy, n-butoxy, isobutoxy, sec-butoxy, tert-butoxy, trifluoromethoxy, methylthio, ethylthio, n-propylthio, isopropylthio, trifluoromethylthio, formyl, acetyl, acetyloxy, methoxycarbonyl, ethoxycarbonyl, carboxyl, amino, methylamino, ethylamino, n-propylamino, isopropylamino, dimethylamino, diethylamino, methylethylamino, di-n-propylamino, diisopropylamino.

The radicals given in the respective definitions and preferred and particularly preferred definitions may, independently of the particular given combination, also be replaced by any radical definitions of other combinations. Moreover, radical definitions from a preferred range may not apply.

The compounds of the formula (I) in which $R^1$ has the general and preferred meanings given above are novel, except for the compounds:

5-iodo-1-[(phenylmethoxy)methyl]tetrazole (CAS RN: 208122-86-5)
5-iodo-1-vinyltetrazole (CAS RN: 141651-20-9)
1-allyl-5-iodotetrazole (CAS RN: 141651-19-6)
1-tert-butyl-5-iodotetrazole (CAS RN: 141651-18-5)
1-ethyl-5-iodotetrazole (CAS RN: 123366-50-7)
5-iodotetrazole (CAS RN: 66924-15-0)
1-methyl-5-iodotetrazole (CAS RN: 33452-18-5)
5-iodo-1-phenyltetrazole (CAS RN: 16484-16-5).

Accordingly, the present invention also provides the novel compounds of the formula (I) and processes for their preparation.

The compounds of the general formula (I) can be prepared by treating tetrazoles of the general formula (II),

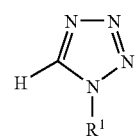

in which
$R^1$ has the general or preferred meaning given above,
with iodine, if appropriate in the presence of a base or a diluent.

In general, the temperature in the processes may be varied within a wide range. As rule, the reaction is carried out between 30° C. and −100° C., preferably at from 0° C. to −90° C.; with very particular preference, the operations are carried out in a range from −20° C. to −80° C.

Suitable bases are, in principle, all customary bases. Strong bases, such as alkali metal amides and alkali metal alkyl compounds, have been found to be particularly advantageous. The following may be mentioned as being very particularly preferred: lithium diisopropylamide, methyllithium, ethyllithium, propyllithium, n-butyllithium, tert-butyllithium, sodium, lithium hexamethyldisilazide.

Suitable for use as diluents are all solvents which do not react with iodine or the base which is added, if appropriate. These solvents preferably include hydrocarbons, such as toluene, xylene or hexane, chlorinated hydrocarbons, such as chlorobenzene, methylene chloride or chloroform, ethers, such as tetrahydrofuran, diethyl ether, methyl tert-butyl ether and dioxane, nitriles, such as acetonitrile, and also DMSO, DMF and NMP.

Alternatively, the compounds of the formula (I) can also be obtained by reacting isocyanides of the formula (III)

in which
$R^1$ is as defined above
with azides and N-iodosuccinimide, if appropriate in the presence of a phase transfer catalyst.

In general, in this process, the temperature can be varied within a wide range; the reaction is usually carried out between −20° C. and 60° C., preferably at from −10° C. to 40° C.

Suitable for use as phase transfer catalysts are all customary phase transfer catalysts, tetraalkylammonium compounds or crown ethers being preferred. Tetrabutylammonium iodide has been found to be particularly suitable.

Suitable for use as solvents are all customary solvents which are not miscible with water and which for their part do not react with the starting materials used. Preference is given to using chlorinated hydrocarbons, particularly preferably chlorobenzene, methylene chloride or chloroform.

The compounds of the general formula (I) can furthermore be obtained by reacting tetrazoles of the general formula (II) in which $R^1$ is as defined above
with iodine, if appropriate in the presence of an acid and, if appropriate, in the presence of an oxidizing agent.

This reaction is generally carried out between 0° C. and 150° C., preferably between 20° C. and 130° C. and particularly preferably between 80° C. and 110° C.

Suitable for use as acids are all customary acids. Preference is given to using acetic acid or sulfuric acid.

Suitable for use as oxidizing agents are all customary oxidizing agents; preference is given to using $KMnO_4$, $HNO_3$, $H_2O_2$ or peracetic acid; very particular preference is given to using $KMnO_4$.

The compounds of the formula (I) have strong microbicidal action and can be used for controlling unwanted microorganisms, such as, for example, fungi, bacteria and algae. The compounds of the formula (I) are preferably used for controlling unwanted microorganisms in the protection of materials.

In the protection of materials, the compounds according to the invention can be used for protecting industrial materials against attack and destruction by unwanted microorganisms.

In the present context, industrial materials are to be understood as meaning non-living materials which have been prepared for use in industry. Industrial materials are, for example, glues, sizes, paper and cardboard, textiles, leather, wood, timber products, paints and plastics, cooling lubricants and other materials which can be attacked or destroyed by microorganisms. Parts of production plants, for example cooling-water circuits, which may be impaired by the multiplication of microorganisms may also be mentioned as industrial materials in the context of the present invention. Industrial materials which are preferably to be protected are glues, sizes, paper and cardboard, leather, wood, paints, plastics, cooling lubricants and heat transfer liquids.

The compounds of the formula (I) according to the invention are particularly suitable for protecting wood, plastics, cooling lubricants, aqueous organic or inorganic dispersions and coating systems, such as paints, varnishes or plasters against attack by microorganisms.

Examples of microorganisms which are capable of brining about degradation of, or change in, the industrial materials and which may be mentioned are bacteria, fungi, yeast, algae and slime organisms. The active compounds of the formula (I) according to the invention preferably act against fungi, in particular molds, wood-discoloring and wood-destroying fungi (Basidiomycetes) and also against slime organisms and bacteria.

Microorganisms of the following genera may be mentioned by way of example:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*,
*Staphylococcus*, such as *Staphylococcus aureus*.

The compounds (I) according to the invention can be used individually or in any mixture with one another for protecting industrial materials.

Depending on their respective physical and/or chemical properties, the active compounds or mixtures thereof can furthermore be converted into customary formulations, such as solutions, emulsions, suspensions, powders, foams, pastes, granules, aerosols and very fine capsules in polymeric substances.

These formulations and compositions are prepared in a known manner, for example by mixing the active compounds with extenders, that is, liquid solvents, liquefied gases under pressure, and/or solid carriers, if appropriate with the use of surfactants, that is emulsifiers and/or dispersants and/or foam-formers. If the extender used is water, it is also possible to use for example organic solvents as auxiliary solvents. Essentially, suitable liquid solvents are: aromatics, such as xylene, toluene or alkylnaphthalenes, chlorinated aromatics or chlorinated aliphatic hydrocarbons, such as chlorobenzenes, chloroethylene or methylene chloride, aliphatic hydrocarbons, such as cyclohexane or paraffins, for example mineral oil fractions, alcohols, such as butanol or glycol and their ethers and esters, ketones, such as acetone, methyl ethyl ketone, methyl isobutyl ketone or cyclohexanone, strongly polar solvents, such as dimethyl formamide and dimethyl sulfoxide, and water. By liquefied gaseous extenders or carriers are meant liquids which are gaseous at ambient temperature and under atmospheric pressure, for example aerosol propellants, such as halogenated hydrocarbons and butane, propane, nitrogen and carbon dioxide. Suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates. Suitable solid carriers for granules are: for example crushed and fractionated natural rocks such as calcite, marble, pumice, sepiolite and dolomite, and synthetic granules of organic and inorganic meals, and granules of organic material such as sawdust, coconut shells, maize cobs and tobacco stalks. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolysates. Suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanin dyestuffs, and trace nutrients such as salts of iron, manganese, boron, copper, cobalt, molybdenum and zinc.

The formulations generally comprise between 0.1 and 95% by weight of active compound, preferably between 2 and 75% by weight.

The present invention further relates to microbicidal compositions based on the compounds according to the invention and comprising at least one solvent or diluent and also, if appropriate, processing auxiliaries and, if appropriate, further antimicrobially active compounds. In this case, the active compounds may be present herein either in dissolved form or as suspensions or emulsions. The solvents or diluents are either water or all customary organic solvents.

The efficacy and the activity spectrum of the active compounds of the formula (I) and of the compositions preparable therefrom, of precursors or of formulations in general can be increased by adding, if appropriate, further antimicrobial compounds, fungicides, bactericides, herbicides, insecticides or other active compounds, so as to widen the spectrum of activity or to obtain particular effects such as, for example, additional protection against insects. These mixtures may have a wider activity spectrum than the compounds according to the invention.

In many cases, synergistic effects are obtained, i.e. the activity of the mixture is greater than the activity of the individual components. The following co-components are found to be particularly favorable:

triazoles such as:
azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazole, penconazole, propioconazole, prothioconazole, simeoconazole, (±)-cis-1-(4-chlorophenyl)-2-(1H-1,2,4-triazol-1-yl)cycloheptanol, 2-(1-tert-butyl)-1-(2-chlorophenyl)-3-(1,2,4-triazol-1-yl)propan-2-ol, tebuconazole, tetraconazole, triadimefon, triadimenol, triapenthenol, triflumizole, triticonazole, uniconazole and their metal salts and acid adducts;

imidazoles such as:
clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chlorophenoxy)-3,3-dimethylbutan-2-one, and their metal salts and acid adducts;

pyridines and pyrimidines such as:
ancymidol, buthiobate, fenarimol, mepanipyrin, nuarimol, pyvoxyfur, triamirol;

succinate dehydrogenase inhibitors such as:
benodanil, carboxim, carboxim sulfoxide, cyclafluramid, fenfuram, flutanil, furcarbanil, furmecyclox, mebenil, mepronil, methfuroxam, metsulfovax, nicobifen, pyrocarbolid, oxycarboxin, Shirlan, Seedvax;

naphthalene derivatives such as:
terbinafine, naftifine, butenafine, 3-chloro-7-(2-aza-2,7,7-trimethyloct-3-en-5-yne);

sulfenamides such as:
dichlofluanid, tolylfluanid, folpet, fluorofolpet, captan, captofol;

benzimidazoles such as:
carbendazim, benomyl, fuberidazole, thiabendazole or their salts;

morpholine derivatives such as:
aldimorph, dimethomorph, dodemorph, falimorph, fenpropidin, fenpropimorph, tridemorph, trimorphamid and their arylsulfonate salts such as, for example, p-toluenesulfonic acid and p-dodecylphenylsulfonic acid;

benzothiazoles such as:
2-mercaptobenzothiazole;

benzothiophene dioxides such as:
N-cyclohexyl-benzo[b]thiophenecarboxamide S,S-dioxide;

benzamides such as:
2,6-dichloro-N-(4-trifluoromethylbenzyl)benzamide, tecloftalam;

boron compounds such as:
boric acid, boric ester, borax;

formaldehyde and formaldehyde-releasing compounds such as:
benzyl alcohol mono(poly)hemiformal, 1,3-bis(hydroxymethyl)-5,5-dimethylimidazolidine-2,4-dione (DMDMH), bisoxazolidine, n-butanol hemiformal, cis-1-(3-chloroallyl)-3,5,7-triaza-1-azoniaadamantane chloride, 1-[1,3-bis(hydroxymethyl-2,5-dioxoimidazolidin-4-yl]-1,3-bis-(hydroxymethyl)urea, dazomet, dimethylolurea, 4,4-dimethyloxazolidine, ethylene glycol hemiformal, 7-ethylbicyclooxazolidine, hexahydro-S-triazine, hexamethylenetetramine, N-hydroxymethyl-N'-methylthiourea, methylenebismorpholine, sodium N-(hydroxymethyl)glycinate, N-methylolchloroacetamide, oxazolidine, paraformaldehyde, taurolin, tetrahydro-1,3-oxazine, N-(2-hydroxypropyl)aminemethanol, tetramethylolacetylenediurea (TMAD);

isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone, N-octylisothiazolin-3-one, 4,5-trimethyleneisothiazolinone, 4,5-benzoisothiazolinone;

aldehydes such as:
cinnamaldehyde, formaldehyde, glutardialdehyde, β-bromocinnamaldehyde, o-phthaldialdehyde;

thiocyanates such as:
thiocyanatomethylthiobenzothiazole, methylenebisthiocyanate;

quaternary ammonium compounds and guanidines such as:
benzalkonium chloride, benzyldimethyltetradecylammonium chloride, benzyldimethyldodecylammonium chloride, dichlorobenzyldimethylalkylammonium chloride, didecyldimethylammonium chloride, dioctyldimethylammonium chloride, N-hexadecyltrimethylammonium chloride, 1-hexadecylpyridinium chloride, iminoctadine tris(albesilate);

iodine derivatives such as:
diiodomethyl p-tolyl sulfone, 3-iodo-2-propynyl alcohol, 4-chlorophenyl-3-iodopropargylformal, 3-bromo-2,3-diiodo-2-propenyl ethylcarbamate, 2,3,3-triiodoallyl alcohol, 3-bromo-2,3-diiodo-2-propenyl alcohol, 3-iodo-2-propynyl n-butylcarbamate, 3-iodo-2-propynyl n-hexylcarbamate, 3-iodo-2-propynyl cyclohexylcarbamate, 3-iodo-2-propynyl phenylcarbamate;

phenols such as:
tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, methyl p-hydroxybenzoate, ethyl p-hydroxybenzoate, propyl p-hydroxybenzoate, butyl p-hydroxybenzoate, octyl p-hydroxybenzoate, o-phenylphenol, m-phenylphenol, p-phenylphenol 4-(2-tert-butyl-4-methylphenoxy)phenol, 4-(2-isopropyl-4-methylphenoxy)phenol, 4-(2,4-dimethylphenoxy)phenol and their alkali metal salts and alkaline earth metal salts;

microbicides with an activated halogen group such as:
bronopol, bronidox, 2-bromo-2-nitro-1,3-propanediol, 2-bromo-4'-hydroxyacetophenone, 1-bromo-3-chloro-4,4,5,5-tetramethyl-2-imidazolidinone, β-bromo-β-nitrostyrene, chloracetamide, chloramine T, 1,3-dibromo-4,4,5,5-tetramethyl-2-imidazolidinone, dichloramine T, 3,4-dichloro-(3H)-1,2-dithiol-3-one, 2,2-dibromo-3-nitrilepropionamide, 1,2-dibromo-2,4-dicyanobutane, halane, halazone, mucochloric acid, phenyl (2-chlorocyanovinyl) sulfone, phenyl (1,2-dichloro-2-cyanovinyl) sulfone, trichloroisocyanuric acid;

pyridines such as:
1-hydroxy-2-pyridinethione (and their Cu, Na, Fe, Mn, Zn salts), tetrachloro-4-methyl-sulfonylpyridine, pyrimethanol, mepanipyrim, dipyrithion, 1-hydroxy-4-methyl-6-(2,4,4-trimethylpentyl)-2(1H)-pyridine;

methoxyacrylates or similar such as:
azoxystrobin, dimoxystrobin, fluoxastrobin, kresoximmethyl, metominostrobin, orysastrobin, picoxystrobin, pyraclostrobin, trifloxystrobin, 2,4-dihydro-5-methoxy-2-methyl-4-[2-[[[[1-[3-(trifluoromethyl)phenyl]ethylidene]amino]oxy]methyl]phenyl]-3H-1,2,4-triazol-3-one (CAS-No. 185336-79-2);

metal soaps such as:
salts of the metals tin, copper and zinc with higher fatty acids, resin acids, naphthenoic acids and phosphoric acid, and as, for example, tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

metal salts such as:

salts of the metals tin, copper, zinc, and also chromates and dichromates, such as, for example, copper hydroxycarbonate, sodium dichromate, potassium dichromate, potassium chromate, copper sulfate, copper chloride, copper borate, zinc fluorosilicate, copper fluorosilicate;

oxides such as:

oxides of the metals tin, copper and zinc, such as, for example, tributyltin oxide, $Cu_2O$, CuO, ZnO;

oxidizing agents such as:

hydrogen peroxide, peracetic acid, potassium persulfate;

dithiocarbamates such as:

cufraneb, ferban, potassium N-hydroxymethyl-N'-methyldithiobarbamate, sodium dimethyldithiocarbamate, potassium dimethyldithiocarbamate, macozeb, maneb, metam, metiram, thiram, zineb, ziram;

nitriles such as:

2,4,5,6-tetrachloroisophthalonitrile, disodium cyanodithioimidocarbamate;

quinolines such as:

8-hydroxyquinoline and their copper salts;

other fungicides and bactericides such as:

bethozaxin, 5-hydroxy-2(5H)-furanone, 4,5-benzodithiazolinone, 4,5-trimethylenedithiazolinone, N-(2-p-chlorobenzoylethyl)hexaminium chloride, 2-oxo-2-(4-hydroxyphenyl) acetohydroxycinnamoyl chloride, tris-N-(cyclohexyldiazeniumdioxy)-aluminum, N-(cyclohexyldiazeniumdioxy)-tributyltin or its potassium salts, bis-N-(cyclohexyldiazeniumdioxy)-copper; iprovalicarb, fenhexamide, spiroxamine, carpropamid, diflumetorin, quinoxyfen, famoxadone, polyoxorim, acibenzolar S-methyl, furametpyr, thifluzamide, methalaxy-M, benthiavalicarb, metrafenon, cyflufenamid, tiadinil, tea tree oil, phenoxyethanol, Ag, Zn or Cu-containing zeolites alone or incorporated into polymeric materials.

Very especially preferred are mixtures with azaconazole, bromuconazole, cyproconazole, dichlobutrazol, diniconazole, diuron, hexaconazole, metaconazole, penconazole, propiconazole, tebuconazole, dichlofluanid, tolylfluanid, fluorfolpet, methfuroxam, carboxin, benzo[b]thiophene S,S-dioxide cyclohexylcarboxamide, fenpiclonil, 4-(2,2-difluoro-1,3-benzodioxol-4-yl)-1H-pyrrole-3-carbonitrile, butenafine, imazalil, N-methylisothiazolin-3-one, 5-chloro-N-methylisothiazolin-3-one, N-octylisothiazolin-3-one, dichloro-N-octylisothiazolinone, mercaptobenthiazole, thiocyanatomethylthiobenzothiazole, thiabendazole, benzoisothiazolinone, N-(2-hydroxypropyl)aminomethanol, benzyl alcohol (hemi)formal, N-methylolchloroacetamide, N-(2-hydroxypropyl)aminemethanol, glutaraldehyde, omadine, Zn-omadine, dimethyl dicarbonate, 2-bromo-2-nitro-1,3-propanediol, 3-iodo-2-propynyl n-butylcarbamate, bethoxazin, o-phthaldialdehyde, 2,2-dibromo-3-nitrilepropionamide, 1,2-dibromo-2,4-dicyanobutane, 1,3-bis(hydroxymethyl)-5,5-dimethylimidazolidine-2,4-dione (DMDMH), tetramethylolacetylenediurea (TMAD), ethyleneglycolhemiformal, p-hydroxybenzoic acid, carbendazim, chlorophen, 3-methyl-4-chlorophenol, o-phenylphenol.

Apart from with the abovementioned fungicides and bactericides, mixtures with a good efficacy are, moreover, also prepared with other active compounds:

insecticides/acaricides/nematicides:

abamectin, acephate, acetamiprid, acetoprole, acrinathrin, alanycarb, aldicarb, aldoxycarb, aldrin, allethrin, alpha-cypermethrin amidoflumet, amitraz, avermectin, azadirachtin, azinphos A, azinphos M, azocyclotin,

*Bacillus thuringiensis*, barthrin, 4-bromo-2(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bistrilfluron, bromophos A, bromophos M, bufencarb, buprofezin, butathiophos, butocarboxim, butoxycarboxim, cadusafos, carbaryl, carbofuran, carbophenothion, carbosulfan, cartap, quinomethionate, cloethocarb, 4-chloro-2-(2-chloro-2-methylpropyl)-5-[(6-iodo-3-pyridinyl)methoxy]-3 (2H)-pyridazinone (CAS-RN: 120955-77-3), chlordane, chlorethoxyfos, chlorfenapyr, chlorfenvinphos, chlorfluazuron, chlormephos, N-[(6-chloro-3-pyridinyl)methyl]-N'-cyano-N-methylethaneimidamide, chlorpicrin, chlorpyrifos A, chlorpyrifos M, cis-resmethrin, clocythrin, clothiazoben cypophenothrin clofentezin, coumaphos, cyanophos, cycloprothrin, cyfluthrin, cyhalothrin, cyhexatin, cypermethrin, cyromazin, decamethrin, deltamethrin, demeton M, demeton S, demeton-S-methyl, diafenthiuron, dialiphos, diazinon, 1,2-dibenzoyl-1(1,1-dimethyl)hydrazine, DNOC, dichlofenthion, dichlorvos, dicliphos, dicrotophos, difethialone, diflubenzuron, dimethoate, 3,5-dimethylphenyl methylcarbamate, dimethyl(phenyl)silylmethyl-3-phenoxybenzyl ether, dimethyl (4-ethoxyphenyl)silylmethyl-3-phenoxybenzyl ether, dimethylvinphos, dioxathion, disulfoton, eflusilanate, emamectin, empenthrin, endosulfan, EPN, esfenvalerate, ethiofencarb, ethion, ethofenprox, etrimphos, etoxazole, etobenzanid, fenamiphos, fenazaquin, fenbutatin oxide, fenfluthrin, fenitrothion, fenobucarb, fenothiocarb, fenoxycarb, fenpropathrin, fenpyrad, fenpyroximate, fensulfothion, fenthion, fenvalerate, fipronil, flonicamid, fluacrypyrim, fluazuron, flucycloxuron, flucythrinate, flufenerim, flufenoxuron, flupyrazofos, flufenzine, flumethrin, flufenprox, fluvalinate, fonophos, formethanate, formothion, fosmethilan fosthiazate, fubfenprox, furathiocarb, halofenocid, HCH, (CAS RN: 58-89-9), heptenophos, hexaflumuron, hexythiazox, hydramethylnon, hydroprene, imidacloprid, imiprothrin, indoxycarb, iodfenfos, iprinomectin, iprobenfos, isazophos, isoamidophos, isofenphos, isoprocarb, isoprothiolane, isoxathion, ivermectin, kadedrin lambda-cyhalothrin, lufenuron, malathion, mecarbam, mervinphos, mesulfenphos, metaldehyde, methacrifos, methamidophos, methidathion, methiocarb, methomyl, metalcarb, milbemectin, monocrotophos, moxiectin, naled, NI 125, nicotine, nitenpyram, noviflumuron, omethoate, oxamyl, oxydemethon M, oxydeprofos, parathion A, parathion M, penfluron, permethrin, 2-(4-phenoxyphenoxy)ethyl ethylcarbamate, phenthoate, phorate, phosalon, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethrum, pyridaben, pyridalyl, pyrimidifen, pyriproxifen, pyrithiobac-sodium, quinalphos, resmethrin, rotenone, salithion, sebufos, silafluofen, spinosad, spirodiclofen, spiromesifen, sulfotep, sulprofos, tau-fluvalinate, taroils, tebufenozide, tebufenpyrad, tebupirimphos, teflubenzuron, tefluthrin, temephos, terbam, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, triazuron trichlorfon, triflumuron, trimethacarb, vamidothion, xylylcarb, zetamethrin;

molluscicides:

fentin acetate, metaldehyde, methiocarb, niclosamide;

herbicides and algicides:

acetochlor, acifluorfen, aclonifen, acrolein, alachlor, alloxydim, ametryn, amidosulfuron, amitrole, ammonium sulfamate, anilofos, asulam, atrazine, azafenidin, aziprotryne, azimsulfuron, benazolin, benfluralin, benfuresate, bensulfuron, bensulfide, bentazone, benzofencap, benzthiazuron, bifenox, bispyribac, bispyribac-sodium, borax, bromacil, bromobutide, bromofenoxim, bromoxynil, butachlor, butamifos, butralin, butylate, bialaphos, benzoyl-prop, bromobutide, butroxydim, carbetamide, carfentrazone-ethyl, carfenstrole, chlomethoxyfen, chloramben, chlorbromuron, chlorflurenol, chloridazon, chlorimuron, chlornitrofen, chloroacetic acid, chloransulam-methyl, cinidon-ethyl, chlorotoluron, chloroxuron, chlorpropham, chlorsulfuron, chlorthal, chlorthiamid, cinmethylin, cinofulsuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhalofop, cyhalofop-butyl, clopyrasuluron, cyclosulfamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn, eglinazine, endothal, EPTC, esprocarb, ethalfluralin, ethidimuron, ethofumesate, ethobenzanid, ethoxyfen, ethametsulfuron, ethoxysulfuron, fenoxaprop, fenoxaprop-P, fenuron, flamprop, flamprop-M, flazasulfuron, fluazifop, fluazifop-P, fuenachlor, fluchloralin, flufenacet, flumeturon, fluorocglycofen, fluoronitrofen, flupropanate, flurenol, fluridone, flurochloridone, fluroxypyr, fomesafen, fosamine, fosametine, flamprop-isopropyl, flamprop-isopropyl-L, flufenpyr flumiclorac-pentyl, flumipropyn, flumioxzim, flurtamone, flumioxzim, flupyrsulfuron-methyl, fluthiacet-methyl, glyphosate, glufosinate-ammonium haloxyfop, hexazinone, imazamethabenz, isoproturon, isoxaben, isoxapyrifop, imazapyr, imazaquin, imazethapyr, ioxynil, isopropalin, imazosulfuron, imazomox, isoxaflutole, imazapic, ketospiradox, lactofen, lenacil, linuron, MCPA, MCPA-hydrazide, MCPA-thioethyl, MCPB, mecoprop, mecoprop-P, mefenacet, mefluidide, mesosulfuron metam, metamifop, metamitron, metazachlor, methabenzthiazuron, methazole, methoroptryne, methyldymron, methyl isothiocyanate, metobromuron, metoxuron, metribuzin, metsulfuron, molinate, manolide, monolinuron, MSMA, metolachlor, metosulam, metobenzuron, naproanilide, napropamide, naptalam, neburon, nicosulfuron, norflurazon, sodium chlorate, oxadiazon, oxyfluorfen, oxysulfuron, orbencarb, oryzalin, oxadiargyl, propyzamide, prosulfocarb, pyrazolate, pyrazolsulfuron, pyrazoxyfen, pyribenzoxim, pyributicarb, pyridate, paraquat, pebulate, pendimethalin, pentachlorophenol, pentoxazone, pentanochlor, petroleum oils, phenmedipham, picloram, piperophos, pretilachlor, primisulfron, prodiamine, profoxydim, prometryn, propachlor, propanil, propaquizafob, propazine, propham, propisochlor, pyriminobac-methyl, pelargonic acid, pyrithiobac, pyraflufen-ethyl, quinmerac, quinocloamine, quizalofop, quizalofop-P, quinchlorac, rimsulfuron sethoxydim, sifuron, simazine, simetryn, sulfosulfuron, sulfometuron, sulfentrazone, sulcotrione, sulfosate, tar oils, TCA, TCA-sodium, tebutam, tebuthiuron, terbacil, terbumeton, terbuthylazine, terbutryn, thiazafluoron, thifensulfuron, thiobencarb, thiocarbazil, tralkoxydim, triallate, triasulfuron, tribenuron, triclopyr, tridiphane, trietazine, trifluoralin, tycor, thdiazimin, thiazopyr, triflusulfuron, vernolate.

The weight ratios of the active compounds in these active compound combinations can be varied within relatively wide ranges.

Preferably, the active compound combinations comprise the active compound in an amount of from 0.1 to 99.9%, in particular from 1 to 75%, especially preferably from 5 to 50%, the remainder to 100% being one or more of the co-components mentioned above.

The microbicidal compositions or concentrates used for protecting the industrial materials comprise the active compound or the active compound combination in a concentration of 0.01 and 95% by weight, in particular from 0.1 to 60% by weight.

The use concentrations of the active compounds or active compound combinations to be used depend on the nature and the occurrence of the microorganisms to be controlled and on the composition of the material to be protected. The optimum rate of application can be determined by test series. In general, the use concentrations are in the range from 0.001 to 5% by weight, preferably from 0.05 to 2.0% by weight, based on the material to be protected.

With the active compounds or compositions according to the invention, it is possible to replace, in an advantageous manner, the microbicidal compositions available to date by more effective compositions. They have good stability and, in an advantageous manner, a broad activity spectrum.

The active compounds can be applied as such, in the form of their formulations or in the use forms prepared therefrom, such as ready-to-use solutions, emulsions, suspensions, wettable powders, pastes, soluble powders, dustable products and granules. Application is carried out in a customary manner, for example by watering, spraying, atomizing, broadcasting, dusting, foaming, spreading, etc.

The examples below are given to illustrate the present invention, without limiting it in any way.

EXAMPLE 1

Route A

5-Iodo-1-butyltetrazole

In an atmosphere of inert gas, 0.032 mol (20 ml) of butyllithium (1.6M in hexane) is added dropwise to a solution, cooled to −78° C., of 0.03 mol (3.78 g) of 1-butyltetrazole in 40 ml of anhydrous tetrahydrofuran such that the temperature of the reaction mixture does not exceed −70° C. The mixture is stirred at this temperature for 30 minutes, and 0.03 mol (7.61 g) of iodine in 10 ml of anhydrous tetrahydrofuran is then added dropwise. After 30 minutes of stirring at this temperature, the reaction mixture is warmed to −30° C., and 1 ml of water is added carefully. The solvent is distilled off under reduced pressure and the residue is taken up in ethyl acetate/water. The aqueous phase is extracted with ethyl acetate and the combined organic phase is washed with sodium thiosulfate solution and saturated sodium chloride solution and dried over sodium sulfate. The residue obtained after distillative removal of solvent under reduced pressure is purified chromatographically (mobile phase: chloroform). This gives 2.2 g (30%) of 5-iodo-1-butyltetrazole of melting point 31-37 C.

EXAMPLE 2

Preparation Route B

5-Iodo-1-phenyltetrazole

With vigorous stirring, a solution of 9.7 mmol (0.63 g) of sodium azide in 10 ml of water and 0.1 g of tetramethylammonium iodide are added to a mixture, cooled to 0° C., of 9.7 mmol (2.18 g) of N-iodosuccinimide in 10 ml of chloroform. After 5 minutes of stirring, a solution of 9.7 mmol (1 g) of phenyl isocyanide in chloroform is added dropwise, and the reaction mixture is stirred at 0° C. for 45 minutes. The reaction mixture is allowed to warm to room temperature, and a further 10 ml of chloroform are added. The phases are separated, and the organic phase is washed 3 times with water, once with saturated sodium thiosulfate solution, again with water and then with saturated sodium chloride solution. After drying over sodium sulfate, the solvent is distilled off under reduced pressure and the residue is recrystallized from ethanol or petroleum (bp.: 80 . . . 110° C.)/ethyl acetate. This gives 0.2 g (8%) of 5-iodo-1-phenyltetrazole of melting point 123-129° C.

The compounds listed in Table 1 were prepared analogously to Examples 1 and 2:

TABLE 1

(Exemplary compounds of the formula 1)

| Example No. | $R^1$ | Preparation route | Physical data |
|---|---|---|---|
| 1 | -n-$C_4H_9$ | A | m.p. = 31-37° C. |
| 2 | phenyl | B | m.p. = 123-129° C. |
| 3 | —$CH_2$—phenyl | A | m.p. = 99-102° C. |
| 4 | —$CH_2$—$CH_2$—phenyl | A | m.p. = 118-120° C. |
| 5 | —$CH_2$—(4-$CH_3$-phenyl) | A | TLC: $R_f$ = 0.29 (EA/hexane = 1:1) |
| 6 | —$CH_2$—(2-$CH_3$-4-F-phenyl) | A | TLC: $R_f$ = 0.41 (EA/hexane = 1:2) |

TABLE 1-continued (Exemplary compounds of the formula 1)

| Example No. | R¹ | Preparation route | Physical data |
|---|---|---|---|
| 7 | 4-methoxybenzyl (−CH₂−C₆H₄−O−CH₃) | A | TLC: $R_f$ = 0.45 (EA/hexane = 1:1) |
| 8 | 2-(4-methoxyphenyl)ethyl (−CH₂CH₂−C₆H₄−O−CH₃) | A | TLC: $R_f$ = 0.43 (EA/hexane = 1:1) |
| 9 | 2-(methoxymethyl)benzyl | A | TLC: $R_f$ = 0.45 (EA/hexane = 1:1) |
| 10 | 1-phenylpropyl (−CH₂−CH(CH₃)−C₆H₅) | A | TLC: $R_f$ = 0.56 (EA/hexane = 1:1) |
| 11 | 4-(trifluoromethyl)benzyl | A | TLC: $R_f$ = 0.43 (EA/hexane = 1:1) |
| 12 | 2-methylbenzyl | A | TLC: $R_f$ = 0.39 (EA/hexane = 1:2) |
| 13 | 3-(trifluoromethyl)benzyl | A | TLC: $R_f$ = 0.41 (EA/hexane = 1:2) |
| 14 | 1-phenylethyl (−CH(CH₃)−C₆H₅) | A | TLC: $R_f$ = 0.3 (EA/hexane = 1:2) |
| 15 | 2-fluorobenzyl | A | m.p = 91° C. |
| 16 | 2-(trifluoromethyl)benzyl | A | m.p = 103° C. |

TABLE 1-continued (Exemplary compounds of the formula 1)

| Example No. | R¹ | Preparation route | Physical data |
|---|---|---|---|
| 17 | —CH₂—CH₂—(2-methoxyphenyl) | A | m.p = 80° C. |
| 18 | —CH₂—CH₂—(2-chlorophenyl) | A | m.p = 96° C. |
| 19 | —CH₂—CH(iPr)—(4-chlorophenyl) | A | m.p = 111° C. |
| 20 | —CH₂—CH₂—(4-fluorophenyl) | A | m.p = 137° C. |
| 21 | —CH₂—CH₂—(2,4-difluorophenyl) | A | m.p = 107° C. |
| 22 | —CH₂—CH₂—(4-methylphenyl) | A | TLC: $R_f$ = 0.41 (EA/hexane) |
| 23 | —CH₂—(2,6-difluorophenyl) | A | m.p = 102° C. |
| 24 | —CH₂—(3-methoxyphenyl) | A | TLC: $R_f$ = 0.40 (EA/hexane) |
| 25 | —CH₂—(3-methylphenyl) | A | m.p = 85° C. |

TABLE 1-continued (Exemplary compounds of the formula 1)

| Example No. | R¹ | Preparation route | Physical data |
|---|---|---|---|
| 26 | 3,5-difluorobenzyl | A | m.p = 135° C. |
| 27 | 3-methylphenethyl | A | m.p < 50° C. |
| 28 | 4-tert-butylbenzyl | A | m.p = 120° C. |
| 29 | 4-propylbenzyl | A | m.p = 79° C. |
| 30 | isohexyl (4-methylpentyl) | A | m.p > 260° C. |
| 31 | 3-fluorobenzyl | A | m.p = 45° C. |
| 32 | 2,2-diphenylethyl | A | TLC: $R_f = 0.49$ (EA/hexane) |
| 33 | 4-fluorobenzyl | A | m.p = 109° C. |
| 34 | 4-(methylthio)benzyl | A | TLC: $R_f = 0.23$ (EA/hexane) |
| 35 | 2-(4-chlorophenyl)-2-ethylbutyl | A | TLC: $R_f = 0.67$ (EA/hexane) |

TABLE 1-continued
(Exemplary compounds of the formula 1)
| Example No. | R¹ | Preparation route | Physical data |
|---|---|---|---|
| 35 | 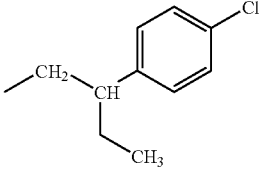 | A | TLC: $R_f$ = 0.34 (EA/hexane) |
| 36 | 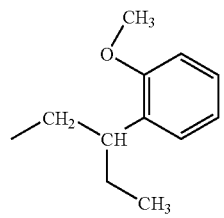 | A | m.p = 123° C. |
| 37 | 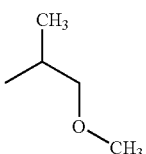 | A | $n_D$ = 1.5323 |
| 38 | 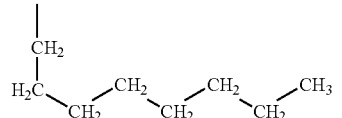 | A | m.p. = 40° C. |
| 39 | 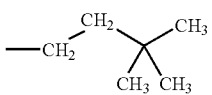 | A | m.p. = 125° C. |
| 40 | 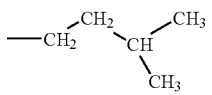 | A | m.p. = 63° C. |
| 41 | 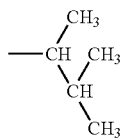 | A | TLC: Rf = 0.6 (tol/EA 5:2) |
| 42 | 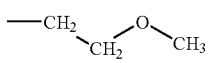 | A | m.p. = 94° C. |
| 43 | 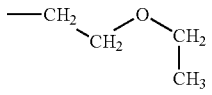 | A | TLC: Rf = 0.6 (tol/EA 5:2) |
| 44 | 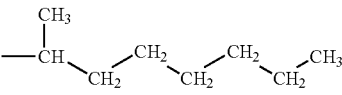 | A | TLC: RF = 0.7 (tol/EA 5:2) |
| 45 | 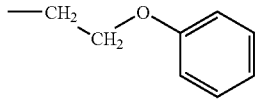 | A | m.p. = 106° C. |

TABLE 1-continued
(Exemplary compounds of the formula 1)
| Example No. | R¹ | Preparation route | Physical data |
|---|---|---|---|
| 46 | 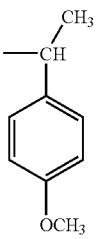 | A | TLC: Rf = 0.55 (tol/EA 5:3) |
| 47 | 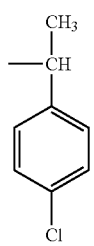 | A | m.p. = 77° C. |
| 48 | 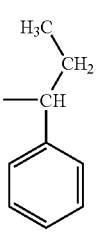 | A | m.p. = 67° C. |
| 49 | 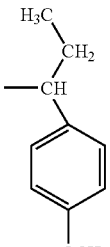 | A | TLC: Rf = 0.75 (tol/EA 5:3) |
| 50 | 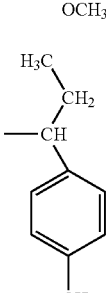 | A | TLC: Rf = 0.8 (tol/EA 5:3) |
| 51 | 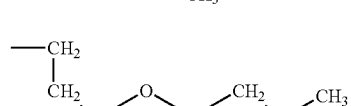 | A | TLC = Rf = 0.6 (tol/EA 5:3) |
| 52 | 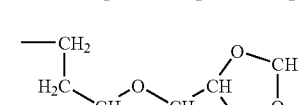 | A | TLC: Rf = 0.25 (tol/EA 5:3) |

TABLE 1-continued
(Exemplary compounds of the formula 1)
| Example No. | R¹ | Preparation route | Physical data |
|---|---|---|---|
| 53 | 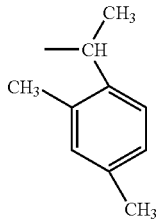 | A | m.p. = 100° C. |
| 54 | 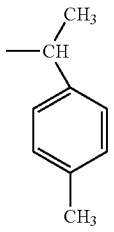 | A | m.p. = 95° C. |
| 55 | 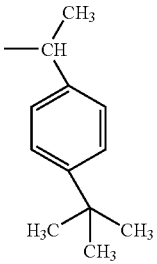 | A | TLC: Rf = 0.75 (tol/EA 5:3) |
| 56 | 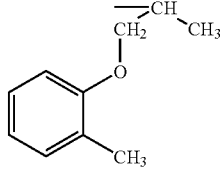 | A | m.p. = 134° C. |
| 57 | 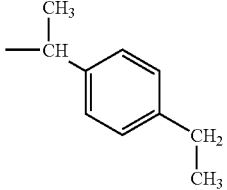 | A | m.p. = 50° C. |
| 58 | 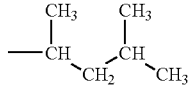 | A | m.p. = 60° C. |
| 59 | 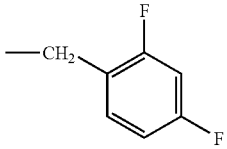 | A | m.p. = 88° C. |

TABLE 1-continued (Exemplary compounds of the formula 1)

| Example No. | R¹ | Preparation route | Physical data |
|---|---|---|---|
| 60 | (2-ethylhexyl group: CH(CH₂CH₃)CH₂CH₂CH₂CH₃) | A | TLC: Rf = I |
| 61 | (2-phenylpropyl: CH(CH₃)CH₂—Ph) | A | TLC: Rf = 0.32 (EA/hexane = 1:1) |
| 62 | (2-(morpholin-4-yl)benzyl) | A | m.p. = 148° C. |
| 63 | (2-methyl-2-phenylpropyl / cumyl-CH₂) | A | m.p. = 130° C. |
| 64 | (isobutyl-CH₂, i.e., 3-methylbutyl: CH₂CH(CH₃)CH₃ shown with extra CH₂) | A | m.p. = 58° C. |
| 65 | —CH₂(CH₂)₇CH₃ (nonyl) | A | m.p. = 52° C. |
| 66 | —CH₂CH₂CH₂CH₂CH₃ (pentyl) | A | m.p. = 32° C. |
| 67 | —CH₂(CH₂)₁₀CH (long alkyl chain) | A | TLC: Rf = 0.19 (EA/hexane = 1:1) |

TABLE 1-continued (Exemplary compounds of the formula 1)

| Example No. | $R^1$ | Preparation route | Physical data |
|---|---|---|---|
| 68 | —CH₂—CH=CH—CH₃ (but-2-enyl group) | A | TLC: Rf = 0.50 (EA/hexane 1:1) |

TLC = Thin-layer chromatogram
EA = Ethyl acetate

Use Example A

To demonstrate the activity against fungi, the minimum inhibitory concentrations (MIC) of agents according to the invention were determined:

In each case, the active compounds according to the invention, in concentrations of from 0.1 mg/l to 5000 mg/l, were added to an agar which had been prepared using malt extracts. After the agar had solidified, it was contaminated with pure cultures of the test organisms listed in Table 3. The MIC was determined after 2 weeks of storage at 28° C. and 60 to 70% relative atmospheric humidity. The MIC is the lowest concentration of active compound at which there is no colonization by the microbial species used. The MIC values are indicated in Table 3 below.

TABLE 2

Minimum inhibitory concentrations (ppm) of compounds of the formula (I) according to the invention

| Example No. | Penicillium brevicaule | Chaetomium globosum | Aspergillus niger |
|---|---|---|---|
| 1 | <1 | 5 | 5 |
| 2 | <40 | <40 | <40 |
| 3 | 5 | 20 | 20 |
| 4 | 5 | 20 | 20 |
| 5 | <40 | <40 | <40 |

Use Example B

To test dispersion coatings for resistance to mold, the following procedure was adopted:

The paint to be tested was applied to both sides of a suitable base. To obtain results which are close to practice, some of the test specimens were rinsed out with running water (24 h, 20° C.) before the test for mold resistance; others were treated with a current of warm fresh air (7 days, 40° C.).

The samples prepared in this way were then placed on an agar nutrient medium, and both samples and nutrient medium were contaminated with fungal spores. After 2-3 weeks storage (29±1° C., 80-90% rel. atmospheric humidity), the samples were compared.

The coating is considered to be permanently mold-resistant if the sample remains free from fungus or at most a slight border infestation can be detected.

For the contamination, fungal spores of the following mold fungi were used, which are known as paint destroyers or are frequently encountered on coatings:

Alternaria tenuis
Aspergillus flavus
Aspergillus niger
Aspergillus ustus
Cindosporum herbarum
Paecilomyces variotii
Penicillium citrium
Aureobasidium pullulans
Stachybotrys chartarum Coatings according to recipe A are mold resistant (even after rinsing out and wind tunnel exposure) if they contain, for example, 1.0% (based on solids) of the compounds of Examples 2, 3, 4 or 5.

| Recipe A: Exterior dispersion paint based on Acroal 290 D (styrene acrylate) | | |
|---|---|---|
| Trade name | Parts by weight | Chemical name |
| Bayer Titan RKB2 | 40 | Titanium dioxide |
| Talkum V58 new | 10 | Magnesium silicate, containing water |
| Durcal 5 | 45 | Calcite CaCO₃ |
| Walsroder MC 3000 S 2% | 30 | Methylcellulose |
| H₂O | 6.5 | Distilled water |
| Calgon N 10% | 3 | Polyphosphate |
| Pigmentverteiler A 10% | 1 | Polyacrylic acid salt |
| Agitan 281, 1:1 in Texanol | 1 | |
| White spirit | 5 | Mixture of aliph. hydrocarbons |
| Butyl glycol acetate | 1.5 | Butyl glycol acetate |
| Acronal 290 D (binder) | 71 | Polyacrylic acid ester |
| Total | 219 | |

Solids content 135.5 = 61.6%.

The invention claimed is:

1. A compound of the formula (I)

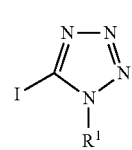

(I)

in which
- R¹ represents hydrogen or in each case optionally substituted alkyl, alkenyl, alkynyl or phenyl, except for the compounds
- 5-iodo-1-[phenylmethoxy)methyl]tetrazole (CAS RN: 208122-86-5)
- 5-iodo-1-vinyltetrazole (CAS RN: 141651-20-9)
- 1-allyl-5-iodotetrazole (CAS RN: 141651-19-6)
- 1-tert-butyl-5-iodotetrazole (CAS RN: 141651-18-5)
- 1-ethyl-5-iodotetrazole (CAS RN: 123366-50-7)
- 5-iodotetrazole (CAS RN: 66924-15-0)1-methyl-5-iodotetrazole (CAS RN: 33452-18-5)
- 5-iodo-1-phenyltetrazole (CAS RN: 16484-16-5)
- 5-iodo-1-1(4-methoxyphenyl)methyl]-1H-tetrazole (CAS RN: 164589-78-0) and
- 5,5'-Bisiodo-1,1'-(ethanediyl)-1H-tetrazole (CAS RN: 141651-17-4).

2. A process for preparing the compound according to claim 1, comprising:
reacting iodine with a tetrazole of the general formula (II)

in which
- R¹ represents hydrogen or in each case optionally substituted alkyl, alkenyl, alkynyl or phenyl.

3. A composition, comprising:
an industrial material, wherein said industrial material comprises the compound according to claim 1.

4. The process according to claim 2, wherein said reacting step is performed in the presence of a base or a diluent.

* * * * *